United States Patent
Ibarra et al.

(10) Patent No.: US 7,173,708 B2
(45) Date of Patent: Feb. 6, 2007

(54) METHOD AND APPARATUS FOR DETECTING DAMAGE IN PLANT PRODUCTS

(75) Inventors: Juan Gutierrez Ibarra, Alta Loma, CA (US); James B. Sheffler, Chino Hills, CA (US); Matias C. Gonzales, Jr., Yucaipa, CA (US); Richard D. Heck, Lucerne Valley, CA (US); Henry A. Affeldt, Jr., Llano, CA (US)

(73) Assignee: Sunkist Growers Inc., Ontario, CA (US)

( * ) Notice: Subject to any disclaimer, the term of this patent is extended or adjusted under 35 U.S.C. 154(b) by 125 days.

(21) Appl. No.: 10/727,491

(22) Filed: Dec. 5, 2003

(65) Prior Publication Data

US 2005/0122524 A1   Jun. 9, 2005

(51) Int. Cl.
*G01N 21/47* (2006.01)
*B07C 5/10* (2006.01)

(52) U.S. Cl. ............... 356/446; 250/223 R; 250/341.8; 250/910; 209/587

(58) Field of Classification Search ........ 356/445–448; 250/223 R, 341.8, 910; 209/587
See application file for complete search history.

(56) References Cited

U.S. PATENT DOCUMENTS

| 4,221,297 A | * | 9/1980 | Aranda Lopez et al. .... 209/576 |
| 5,164,795 A | * | 11/1992 | Conway ..................... 356/407 |
| 5,487,472 A | * | 1/1996 | Satake et al. ............... 209/581 |
| 5,791,497 A | * | 8/1998 | Campbell et al. .......... 209/577 |

* cited by examiner

*Primary Examiner*—Richard A. Rosenberger
(74) *Attorney, Agent, or Firm*—Sughrue Mion, PLLC

(57) ABSTRACT

A method and apparatus of sorting plant products based on damage to the plant products is disclosed. A beam emitter emits an illumination light toward the outer surface of a plant product. A beam detector detects substantially a single wavelength of a reflected light produced by the plant product responsive to the illumination light. A control unit determines at least one of a presence, an amount, and a severity of damage responsive to the reflected light. The control unit assigns a damage category to the plant product responsive to the determination of damage.

53 Claims, 3 Drawing Sheets

METHOD AND APPARATUS FOR DETECTING DAMAGE IN PLANT PRODUCTS

BACKGROUND OF THE INVENTION

The present invention relates generally to a method and apparatus for detecting damage in plant products and, more particularly, to a method and apparatus for citrus fruit decay detection using substantially a single wavelength of light and sorting the plant products by damage categories.

In the plant product processing industry, a quantity of plant products are often stored and/or shipped together while packed into an enclosed space. If one or more of the packed plant products is damaged by even a small amount of decay, the close packing often allows that decay to spread quickly to other plant products. In addition, pre- or post-harvesting mechanical damage to the plant products, such as punctures or cuts, may allow decay to afflict the plant products more quickly than if the outer surface of the plant products were whole and undamaged. Since decayed plant products are unhealthy and unattractive to the consumer, government regulations require a minimal amount of decay in plant products provided for human consumption. Decay can be very expensive for producers of plant products since entire shipments of plant products may be refused by the retailer or consumer due to the presence of decay above the government-mandated levels.

It is critically important for processors and packagers of plant products to detect, and even distinguish among, decay, pre-harvest mechanical damage, post-harvest mechanical damage, blemishes, stems, blossoms, firmness, or water content (hereafter referenced generally as "damage") to the plant products before those products are packaged for shipping, at least partially so that a small spot of decay on one plant product does not allow decay to spread throughout the shipment. Traditionally, damage inspections were done by trained human inspectors. However, even the most conscientious inspector has moments of inattention and the inspector's visual acuity can be dulled by long hours of repetitive and uninteresting inspection work. Moreover, damage can be extremely difficult for a human inspector to see because of inefficient viewing angles, extremely small areas/amounts of damage, or damage that is a similar color to the natural color of the plant product.

Many different schemes have been proposed for detecting damage or foreign matter in plant products. For example, U.S. Pat. No. 3,930,994, issued Jan. 6, 1976 to Conway et al., discloses a system which uses infrared light to penetrate a plant product and thereby produce an assessment of internal damage. However, due to natural variations in size, shape, and density of plant products of even the same species, the transmittal of light through the plant product is not uniform enough to provide reliable results and any such inspection system must discard many "good" plant products to be sure of eliminating a large percentage of "bad" plant products.

An alternate scheme and device is presented in U.S. Pat. No. 5,487,472, issued Jan. 30, 1996 to Satake et al. (hereafter referenced as '472). The '472 device uses reflected light to detect damage to the outer surface of a plant product. The reflected light is of multiple wavelengths specially chosen to highlight damage to the plant product. Unfortunately, the use of a spectrum or multiple wavelengths adds greatly to the cost, size, and complexity of this type of inspection system and also increases the chances of an acceptable blossom, stem, or natural blemish on the plant product causing a false positive damage scan and resultant waste of good plant products. Additionally, the '472 device does not provide a thorough inspection of substantially the entire surface of the plant product because the plant product passes through the inspection system while lying on a conveyor belt, so the belt blocks part of the plant product from view.

The present invention is directed to overcoming one or more of the problems as set forth above.

SUMMARY OF THE INVENTION

In an embodiment of the present invention, a method of sorting plant products based on damage to the plant products is disclosed. The method includes the steps of: emitting an illumination light toward the outer surface of a plant product; detecting substantially a single wavelength of a reflected light produced by the plant product responsive to the illumination light; determining at least one of a presence, an amount, and a severity of damage responsive to the reflected light; and assigning a damage category to the plant product responsive to the determination of damage.

In an embodiment of the present invention, an apparatus for sorting plant products based on damage to the plant products is disclosed. The apparatus includes a first beam emitter, a first beam detector, and a control unit. The first beam emitter provides a first illumination light to a plant product. The first beam detector detects substantially a single wavelength of first reflected light from the plant product and responsively produces a first reflection signal. The control unit receives at least one first reflection signal and responsively assigns a damage category to the plant product. The control unit determines at least one of a presence, an amount, and a severity of damage responsive to the first reflection signal and assigns the damage category to the plant product responsive to the determination of damage.

In an embodiment of the present invention, an apparatus for sorting plant products based on damage is disclosed. The apparatus includes means for determining, responsive to substantially a single wavelength of light, at least one of a presence, an amount, and a severity of damage to a surface of the plant product; and means for sorting the plant products into one of two or more damage categories responsive to the determination of damage.

In an embodiment of the present invention, an apparatus for scanning a plant product to detect damage to the plant product is disclosed. The apparatus includes at least one beam emitter, at least one beam detector, and a control unit. The beam emitter provides an illumination light to the plant product. The beam detector detects a reflected light from the plant product and responsively produces at least one reflection signal. The control unit receives the at least one reflection signal and responsively generates a plant product image. The reflected light has substantially a single wavelength and damage to the plant product is detected responsive to the plant product image.

BRIEF DESCRIPTION OF THE DRAWINGS

For a better understanding of the invention, reference may be made to the accompanying drawings in which.

DETAILED DESCRIPTION OF THE INVENTION

Figure 1:
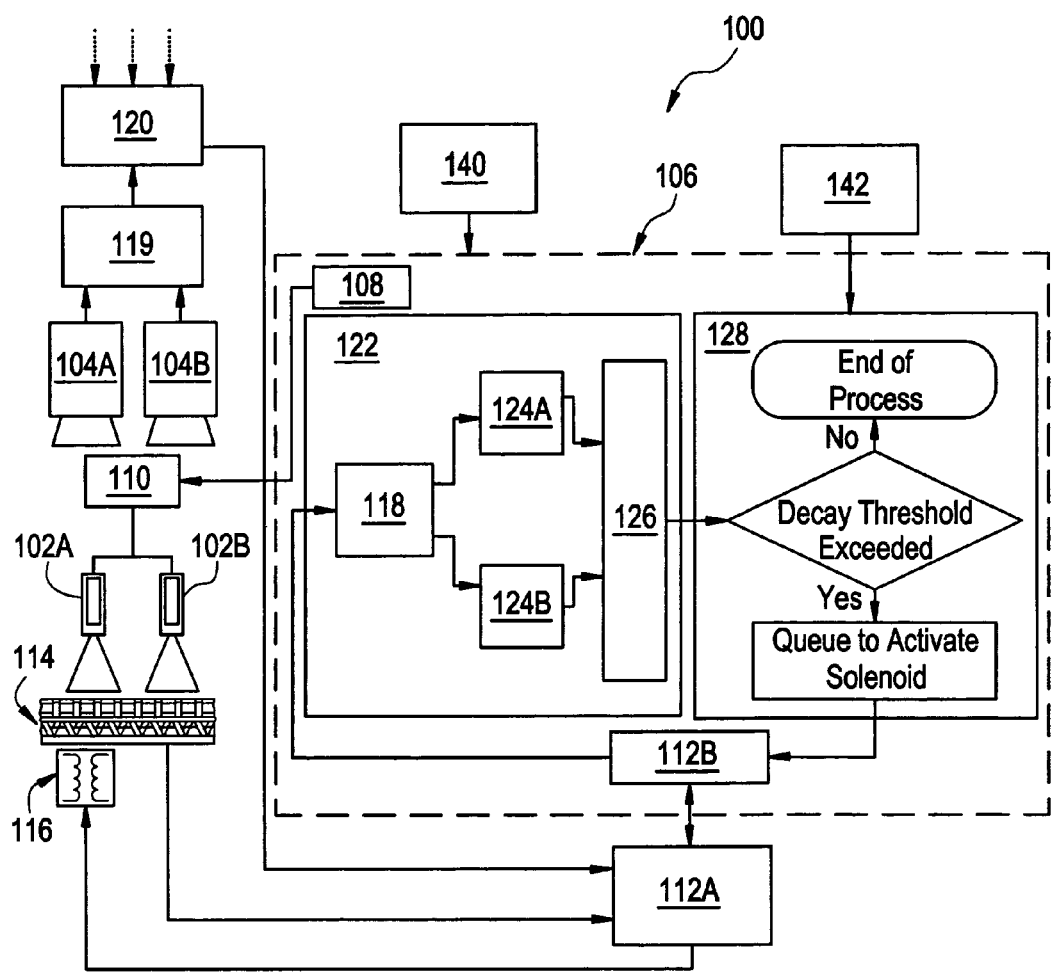
FIG. 1 is a block diagram of a preferred embodiment of the present invention.

A preferred embodiment of the present invention provides a method and apparatus for detecting damage to plant products and sorting the plant products based on the damage determination. The plant product may be any suitable non-citrus fruit, vegetable, legume, citrus fruit, or the like, but will be generally described herein as a "plant product". FIG. 1 depicts an inspection system 100 according to an embodiment of the present invention. The inspection system 100 includes at least one beam emitter 102 and at least one beam detector 104. The embodiment shown in FIG. 1 includes two beam emitters 102A, 102B and two beam detectors 104A, 104B, but any suitable number of beam emitters 102 or beam detectors 104 may be used with the present invention. Moreover, the beam emitters 102 and beam detectors 104 need not be provided in matched pairs as shown in FIG. 1. For example, a single beam emitter 102 could bathe a target area, or inspection site, with a broad beam and multiple beam detectors 104 could each monitor a predetermined portion of the inspection site. Thus, multiple images may be generated of the same piece of plant product for later assembly and processing.

The beam emitters 102 may be at least one of a laser, a light-emitting diode, a broad-spectrum lamp, a broad-spectrum lamp equipped with a filter, or any other suitable beam emitter 102 or combination of emitters 102. The emitter(s) 102 can optionally be equipped with additional optics (lenses, polarizers, or the like). Preferably the beam emitter 102 is an infrared laser of the diode type having a wavelength output of substantially a single wavelength.

As is known in the art, a "single-wavelength laser" will actually emit light in a band of wavelengths that have a power spectrum that will be at a peak power at substantially the recited wavelength and will have power levels that fall off from the peak. Moreover, the recited wavelength is also specified within normal industry tolerances, and provides no impediment to the present invention. Therefore, a laser having an output of "substantially" a single wavelength is permitted to also produce a limited amount of light having wavelengths different from the single wavelength without departing from the spirit and scope of the present invention, as defined by the claims.

Additionally, it is preferred that the single wavelength be in the range of 900 nm to 1100 nm, and more particularly 980 nm since experimentation has shown that such a wavelength possesses desirable characteristics, to be discussed below. Optionally, the beam emitters 102 are adapted to emit a narrow beam which illuminates substantially along a line perpendicular to the direction of emission, by scanning a beam along a predetermined path, by passing the beam through an optical device to concurrently take the form of a line, or by any other suitable method In general, the beam emitter may vary with the type of detector 104 but should provide suitable illumination for the field of view ("FOV") of the beam detector(s) 104.

The beam detectors 104 may be at least one of a photodiode, a photosensor, a camera, a camera equipped with a filter, a CCD sensor, or any other suitable type of detector 104 or combination of detectors 104. The detector(s) 104 can optionally be equipped with additional optics (lenses, polarizers, filters, a photometric unit such as a grate or prism, or the like). In the event that a spectrum-producing beam emitter 102 is used, the beam detectors 104 may be equipped with a filter so that only light of substantially a single wavelength, as set forth above, is detected by the beam detectors 104. Optionally, the beam detectors 104 are adapted to detect a beam substantially along a one-dimensional detection line—for example, the beam detector 104 could be a "line scan" camera. The inspection system 100 will be discussed herein as detecting a beam substantially along such a detection line. Alternately, the FOV of the beam detector 104 could be a two-dimensional area—such as when an "area scan" camera is used as the beam detector 104—with suitable changes to the software and optics of the inspection system 100. One of ordinary skill in the art could readily utilize an area scan beam detector 104 in place of the discussed line scan beam detector 104 without departing from the spirit and scope of the present invention.

The information from the beam detectors 104A,104B can be combined into a single data stream through the use of such known devices as a multiplexer 119. The combination of emitters 102A,102B, detectors 104A,104B, multiplexer 119, conveyor system 114 and sorting system 116 may relate to a single processing lane. Optionally and as shown by the dashed arrows in FIG. 1, the information from multiple lanes, each comprising emitters, detectors and multiplexers, can be combined or partially processed through the use of a known concentrator 120 in much the same way as the single lane discussed herein.

A control unit 106 provides interface and processing functions to the rest of the inspection system 100 in any suitable manner, preferably by including a processor, a memory (optionally integrated with the processor), and at least one software instruction. Suitable software instructions may include programming for: beam emitter 102 control, beam detector 104 control, reflection signal control, reflection signal combining, reflection signal analysis, image generation, damage assessment, damage category assignation, plant product routing, or any other suitable functions. The control unit 106 may be located near the beam emitters 102 and beam detectors 104 or may be remotely located. The control unit 106 may be dedicated to a given inspection system 100, inspection site, or processing line, or may be centralized to serve multiple inspection systems 100, inspection sites, or processing lines. In addition, though the control unit 106 is depicted in FIG. 1 as being a single unit within the dashed line, there is no requirement in the present invention that the control unit 106 be assembled as an integrated whole or be assembled in such a way as to exclude components not shown or shown outside the dashed line. For example, a portion of the signal processing function could be provided within the beam detectors 104, consistent with the present invention.

In the embodiment depicted in FIG. 1, the control unit 106 includes a Control Area Network (CAN) card 108, which provides instructions to a gain control 110 to activate the beam emitters 102. The control unit 106 also includes at least one interface 112, comprising an external portion 112A and a portion 112B that is internal to the control unit, which passes information back and forth in a known manner between the control unit 106 and one or more other components of the inspection system 100. In FIG. 1, the interface 112 conveys information from the beam detectors 104 (via multiplexer 119 and concentrator 120, as optionally implemented) and a conveyor system 114 to the control unit 106, and forwards information from the control unit 106 to a sorting system 116. On the basis of the foregoing arrangement, as would be understood by one skilled in the art, multiple beam detectors 104 and beam emitters 102 are used at the same or different inspection sites, at a single or multiple lanes, to inspect the same or different individual plant product(s) 230, and the control unit 106 is provided with the software and hardware necessary to differentiate between the individual inspection sites and/or plant product(s) 230 in order to accurately track damage to the plant product(s) 230. For a single plant product 230, several images may be taken, each image forming a packet, and the several packets for a single piece of plant product 230 that are combined by the multiplexer 119 into a single data stream would be processed by the control unit 106. For plant product 230 in multiple lanes, the data stream input to a concentrator 120, that receives similar multiplexed outputs from multiplexers 119, would be forwarded to the control unit 106 for further processing.

The control unit 106 in the embodiment shown in FIG. 1 also includes a Digital Signal Processing (DSP) card 122 for collecting, processing, and/or facilitating the display of information obtained from the beam detectors 104 and processed. When the information from multiple beam detectors 104 is multiplexed together, as shown in FIG. 1, the DSP card 122 includes demultiplexing software 118 which breaks apart the concentrated and multiplexed information from the beam detectors 104 in one or more lines into a series of reflection signals, each corresponding to a beam detector 104, that are stored individually, temporarily or permanently, in any desired form as stored reflection signals 124A, 124B. For example, the stored reflection signals 124A, 124B may be data arrays, digital images, or other suitable information groupings, and/or may be held in short-term memory for immediate processing or in long-term memory for archival or other purposes.

The stored reflection signals 124A, 124B are then processed using an image processing algorithm 126, which analyzes the stored reflection signals 124A, 124B and renders a number to be compared with thresholds in a decision module 128 by way of example, to complete the inspection process for a given plant product 230. In the exemplary logic 128, a determination is made on whether a decay threshold is exceeded and, if not, the process ends. One or more thresholds may be set for various decisions. If the one (or more) threshold(s) is exceeded, one or more solenoid activation signals may be generated and forwarded to the interface 112. Thus, depending upon the result of the determination of damage for a given piece of plant product 230, the control unit 106 may pass one or more signals to the sorting system 116 to route that piece of plant product 230 to one of two or more predetermined locations, such as continued normal processing, a discard bin, or any other desired destinations.

Figure 2:
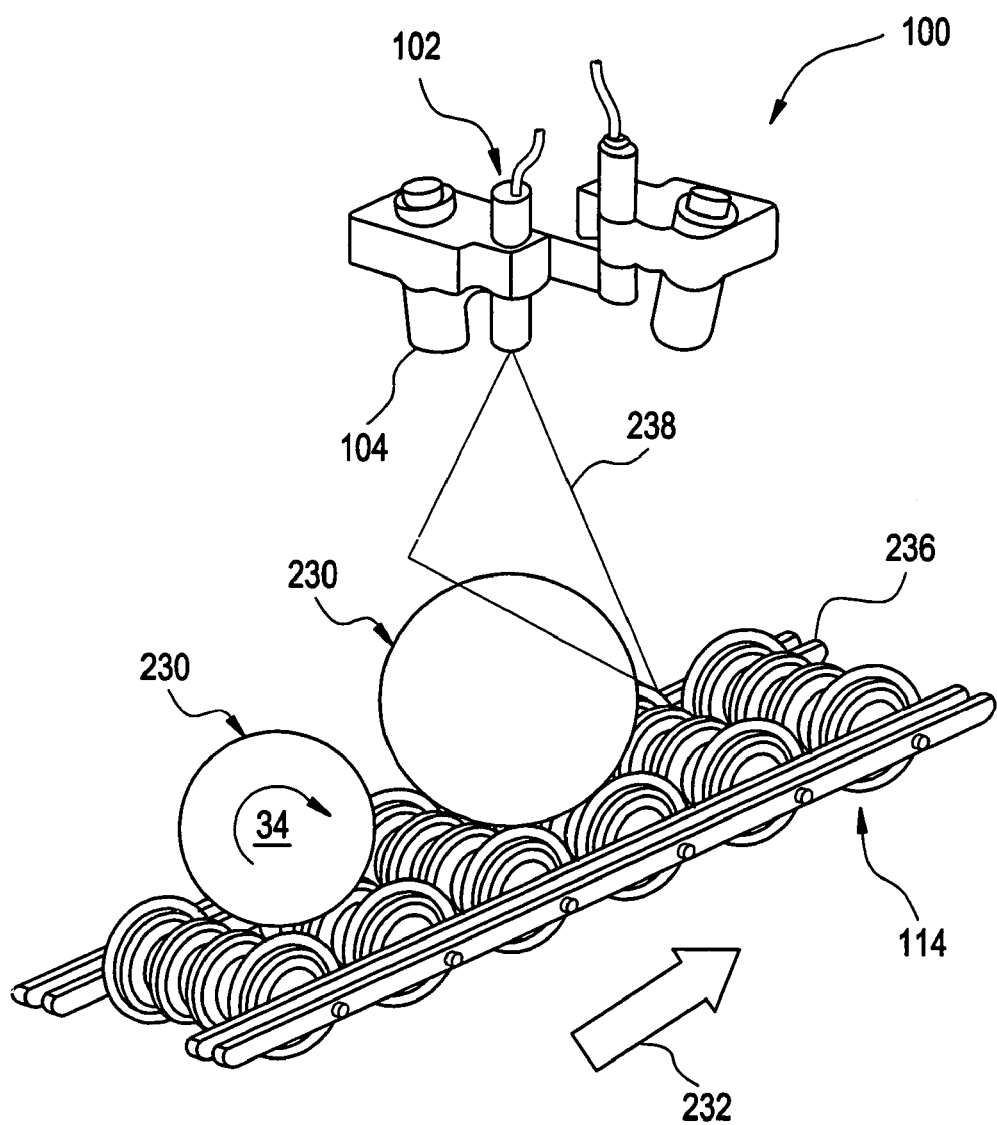
FIG. 2 is a perspective view of a portion of a preferred embodiment of the present invention.

FIG. 2 is a partial perspective view of an embodiment of the present invention. A portion of the inspection system 100 is shown, including beam emitters 102 and beam detectors 104. The relative arrangements of the beam emitters 102 and beam detectors 104 need not be as depicted in FIG. 2 and suitable spacing and relative angles may readily be determined experimentally for a given application of the inspection system 100. The conveyor system 114 moves the plant product 230 in a travel direction 232 (for ease of description, the travel direction 232 is defined as being a "longitudinal" direction with respect to the inspection system 100) along a product line in any suitable manner, past the beam emitters 102 and the beam detectors 104. Examples of suitable conveyor systems 114 include rollers (as shown), belts, water tanks, pushers, gravity systems, cups, static surfaces such as ramps or tables, or any other conveyor systems 114 which allow for the desired scanning; the exact mechanism of providing the plant product 230 to the inspection system 100 is not crucial to the present invention.

Preferably, the conveyor system 114 also rotates each plant product 230 in a rotation direction 234 about an axis perpendicular, or lateral, to the travel direction 232 and at a predetermined rotation rate as the plant product 230 moves in the travel direction 232, in order to expose substantially the entire outer surface of the plant product 230 to the beam emitters 102 and beam detectors 104. Alternately, only a portion of the outer surface of the plant product 230, such as an end or side, can be exposed to the beam emitters 102 and beam detectors 104, and a suitable conveyor system 114 could be used to orient the plant product 230 for the desired view.

In the embodiment shown in FIG. 2, driven rollers 236 rotate the plant product 230 in the rotation direction 234. The rollers 236 also serve to separate plant product 230 that may be delivered in a group such that each plant product 230 being inspected is readily identifiable by roller 236 location, thereby providing the sorting system 116 with a way to track and sort each individual plant product 230 for routing to a predetermined location.

The beam emitter 102 emits an illumination light 238 toward the outer surface of the plant product 230 being inspected. Preferably and as shown in FIG. 2 and discussed above, the illumination light 238 is a narrow beam provided in a line perpendicular to the travel direction 232 of the plant product 230. The plant product 230 then produces a reflected light (not shown) responsive to the illumination light 238. Preferably the reflected light is reflected by substantially the outer surface of the plant product 230, but depending upon the wavelength of the illumination light 238, reflected light could be reflected at least partly from portions of the plant product 230 which are internal to a strictly defined plant product/air interface, such as the zest or inner rind of the plant product 230. Regardless, light reflected from these nominally inner portions of the plant product 230 is considered to be "reflected light" for purposes of the present invention since the wavelength of the illumination light 238 can be readily chosen to minimize or maximize this effect for a desired inspection system 100 application. In addition, the reflected light could be reflected from a predetermined portion of the plant product 230 which is not substantially the outer surface of the plant product 230, such as an end region or some other limited portion of the outer surface, as desired for a particular application of the present invention.

The beam detector 104 detects substantially a single wavelength of the reflected light, possibly because the illumination light 238 has substantially a single wavelength or because the beam detector 104 is equipped with a filtering device—the exact mechanism of obtaining the substantially single wavelength is not essential to the present invention. In a preferred embodiment for detecting decay in citrus fruit, a wavelength of 980 nm is provided because (1) a surface with decay reflects such light in a distinctive manner as compared to a surface without decay, and (2) commercial lasers with beams substantially of 980 nm are relatively inexpensive and readily available. The beam detector 104 passes information on the reflected light to the control unit 106; the information is characterized here for simplicity as a reflection signal 124 produced by the beam detector 104 and transmitted to the control unit 106.

The FOV of the beam detector 104 is associated with an inspection site. An inspection system 100 may have multiple inspection sites, with each corresponding to the FOV of a different beam detector 104. Note that the FOVs may overlap partially or substantially without departing from the present invention. Multiple inspection sites may allow substantially the entire outer surface of each plant product 230 to be inspected more thoroughly and/or efficiently than with just one inspection site, but the multiplicity requires more complicated programming of the control unit 106. For example, the accumulated detected reflected narrow beams must be assembled and integrated for all inspection sites to form one or more images of a single plant product 230.

The reflected light bears a particular relationship to any damage which might be present on or near the outer surface of the plant product 230. Namely, depending upon the single wavelength chosen, damage reflects a markedly different amount of the illumination light 238 than does an undamaged outer surface of the plant product. For descriptive purposes, damage will be assumed to reflect less illumination light 238 than the undamaged outer surface, thereby creating a "dark spot" in an image based on the reflected light. Note that, though the reflected light will be discussed in terms of an "image", a literal image need not be generated by the control unit 106. For example, a less-than-expected return of reflected light could produce a low enough value of the reflection signal 124 that the control unit 106 can accurately determine the presence of damage on the plant product 230 without a visual image being processed.

Once the control unit 106 has received at least one reflection signal 124, at least one of a presence, an amount, and a severity of damage to a particular plant product 230 being inspected is determined responsive to the reflected light. "Damage" is predefined by an operator, preferably by choice of wavelength for the reflected light, and may include one or more of decay, pre-harvest mechanical damage, post-harvest mechanical damage, and blemishes. The inspection system 100 may also or instead detect such natural properties of the plant product 230 as stems, blossoms, firmness, water content, or any other desired traits—though these properties are not necessarily "damage" in the traditional sense, the term "damage" as used in the description and claims of the present invention is defined as including these traits (along with the aforementioned decay, pre-harvest mechanical damage, post-harvest mechanical damage, and blemishes), for ease of description.

Optionally, the control unit 106 can assign a damage category to each plant product 230 responsive to the determination of damage. Preferably, the control unit 106 then directs the plant product 230 to one of two or more predetermined locations—for example, a discard bin, a first quality line, a non-food quality line, or other suitable locations—responsive to the damage category. For example, if less than 3% of the plant product 230 surface contains damage, the plant product 230 could be allowed to proceed to packing, whereas plant product 230 containing damage on 3–10% of the surface is sent to a juicing line and plant product 230 with more than 10% damage is sent to a discard bin. Preferably, the damage categories are adjusted to minimize the amount of good plant product 230 sent to the discard bin because of field conditions or peculiarities of the inspection system 100, with adjustments possibly being made during operation of the inspection system 100 through a technician's interface 140 or user interface 142 to the control unit 106 shown in FIG. 1. The listed percentages and numbers of the above scenarios are purely exemplary, and can be readily determined experimentally for a given application of the inspection system 100. The choice of a specific sorting system 116 is also not essential to the present invention and can be readily provided by one of ordinary skill in the art.

In an embodiment of the present invention wherein an image is generated of the plant product 230, the control unit 106 receives multiple reflection signals 124, with each reflection signal 124 corresponding to a "slice" view of the outer surface of the plant product 230 taken along the detected line of reflected light. The control unit 106 then combines these multiple reflection signals 124, facilitated by the motion of the plant product 230 in the rotation direction 234, into an image of substantially the entire outer surface of the plant product 230. Preferably, the reflection signals 124 are stored and then combined, once the control unit 106 has scanned substantially the entire outer surface of the plant product 230, to produce a visual image of that particular plant product 230 for determination of damage. Programming which provides an integration of several separate detected images into a single image, or multiple images, for comparison or judgment may be readily achieved by one skilled in the art on the basis of the provided disclosures without undue experimentation. Alternately another suitable method could be used, such as summing the values of the reflection signals 124, with the damage category of that plant product 230 determined by the final total of the sum. In any instance, the control unit 106 is equipped to: detect when each individual plant product 230 has entered the inspection site, collect at least one reflection signal 124 corresponding to that plant product 230, detect when a surface of the plant product has been scanned by the beam detectors 104, and make a determination of the quantity of damage on the surface of the plant product. In light of the present limitations of optical components and processing lines, it is envisioned that the above steps will preferably be performed in 80 ms or less to allow for smooth flow of the plant product 230 through the system. However, the speed of performance of the inspection system 100 is not essential to the present invention. The inspection process could be performed with the plant product 230 traveling at any speed—or even remaining stationary—with respect to the inspection system 100.

Figure 3:
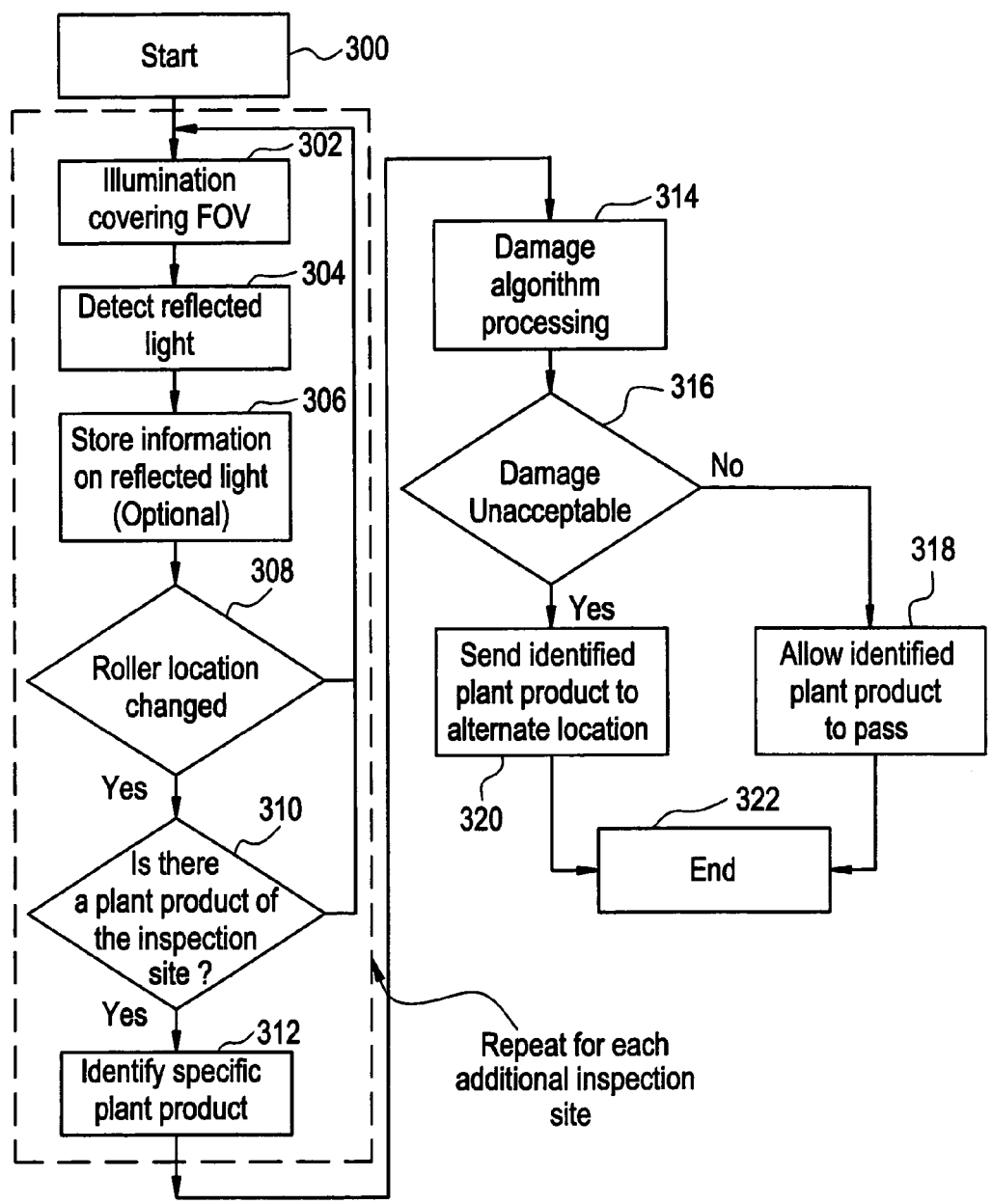
FIG. 3 is a flowchart of the logic of a preferred embodiment of the present invention.

FIG. 3 depicts a flowchart of the logic of the present invention. Control begins at start block 300 and passes to first control block 302, where an illumination light is provided to the FOV of the beam detector 104. Control then passes to second control block 304, where the beam detector 104 detects the reflected light. Control then proceeds to third control block 306, where an optional (as shown by the dotted line) step of storing information on the reflected light is performed, if desired.

Whether or not the logic of third control block 306 is performed, control then proceeds to first decision block 308, where the location of a roller 236 of the conveyor system 114 is compared to a previously observed position. If the location of the roller 236 has not changed, control loops back to the start block 300 and the logic of FIG. 3 is repeated. If the location of the roller 236 has changed, then control proceeds to second decision block 310.

At second decision block 310, the presence or absence of a plant product 230 at a predetermined inspection site (defined by the specific configuration of a given inspection system 100) is evaluated. If there is no plant product 230 at the inspection site, control returns to start block 300. However, if a plant product 230 is present at the inspection site, control proceeds to fourth control block 312, where that specific plant product 230 is identified.

The logic of FIG. 3, from the first control block 302 through the second decision block 312 (as indicated by the dashed line), is repeated for each inspection site of the inspection system 100. Therefore, multiple beam emitters 102 and beam detectors 104 can be provided, and can inspect the same or different plant products 230 concurrently, while still falling under the scope of the attached claims. One of ordinary skill in the art will be able to readily provide software and hardware to carry out any inspection system 100 using the present invention and is not restricted to the precise inspection system 100 shown and discussed herein by way of example.

From fourth control block 312, control proceeds to fifth control block 314, where the determination of damage of the identified plant product 230 is performed, according to the chosen damage algorithm. The determination may be made by comparing against a standard, a reference image, a threshold value set in memory, or another suitable scheme. A variety of judgment techniques are known and a preference of one over another may depend upon the plant product being examined. As would be understood by one skilled in the art, one or more parameters and/or thresholds may be used in the analysis and decision process.

From fifth control block 314, control proceeds to third decision block 316, where the acceptability of the damage detected is determined. If there is no damage or if the damage is acceptable, the identified plant product 230 is allowed to pass the inspection system 100 at sixth control block 318. However, if the damage is unacceptable, control proceeds to seventh control block 320 and the identified plant product 230 is sent to an alternate location instead of being allowed to pass through to the normal processing procedure. From either of sixth or seventh control blocks 318,320, the processing for a single piece of plant product ends at end block 322 and a new process for a next piece of plant product will begin at block 300.

The logic of FIG. 3 may be repeated as necessary for desired functioning of the inspection system 100. In addition, multiple identified plant products 230 can be at different stages of the logic at the same time, with the control unit 106 tracking each individual identified plant product 230 and processing the multiple identified plant products 230 in parallel. Finally, known safeguards against failure of the inspection system 100 because of faulty components, flawed logic, or other known causes of harm to electronic systems would be implemented as needed without effecting the operation of the present invention.

While aspects of the present invention have been particularly shown and described with reference to the preferred embodiment above, it will be understood by those skilled in the art that various additional embodiments may be contemplated without departing from the spirit and scope of the present invention. For example, the determination of damage could be made before the entire outer surface of the plant product 230 is scanned; the control unit 106 could have differing hardware, software, or configuration than that described; or a different damage determination scheme (such as a single threshold damage level triggering discard) could be utilized. However, a device or method incorporating such an embodiment should be understood to fall within the scope of the present invention as determined based upon the claims below and any equivalents thereof. Other aspects, objects, and advantages of the present invention can be obtained from a study of the drawings, the disclosure, and the appended claims.

What is claimed is:

1. A method of sorting plant products based on damage to the plant products, the method comprising the steps of:
   emitting an illumination light toward an outer surface of a plant product to produce a narrow beam defining a line of light on said outer surface that is perpendicular to a travel direction of the plant product;
   detecting with a narrow field of view overlapping said line of light on said outer surface substantially a single wavelength of a reflected light produced by the plant product responsive to the illumination light without detecting light at other wavelengths;
   rotating the plant product about an axis parallel to said direction of travel and at a predetermined rotation rate;
   determining, in response to reflected light from a plurality of detected narrow beams accumulated sequentially as the plant product is moved and rotated in a direction of travel, at least one of a presence, an amount, and a severity of damage responsive to the reflected light solely at a single wavelength;
   assigning a damage category to the plant product responsive to the determination of damage; and
   sorting a plant product on the basis of an assigned category.

2. The method of claim 1, wherein the step of emitting an illumination light includes:
   emitting an illumination light having substantially a single wavelength.

3. The method of claim 1, wherein the step of determining at least one of a presence, an amount, and a severity of damage responsive to the reflected light includes:
   determining at least one of a presence, an amount, and a severity of at least one of decay, pre-harvest mechanical damage, post-harvest mechanical damage, blemish, stems, blossoms, firmness, or water content of the plant product.

4. The method of claim 1, including the steps of:
   storing information on the reflected light;
   generating an image of a surface of the plant product responsive to the stored information; and
   assigning the damage category to the plant product responsive to the generated image.

5. The method of claim 1, including the step of:
   directing the plant product to one of two or more predetermined locations based upon the damage category of the plant product.

6. The method of claim 1, wherein the plant product is at least one of a non-citrus fruit, a vegetable, a legume, and a citrus fruit.

7. The method of claim 1, wherein the single wavelength is substantially within the range of 900 nm to 1100 nm.

8. The method of claim 1, wherein damage to the plant product reflects less of the illumination light as reflected light than does an undamaged outer surface of the plant product.

9. The method of claim 1, wherein the steps of determining at least one of a presence, an amount, and a severity of damage responsive to the reflected light; and assigning a damage category to the plant product responsive to the determination of damage are accomplished within a time interval of 80 ms or less.

10. The method of claim 1, wherein the step of detecting substantially a single wavelength of a reflected light produced by the plant product responsive to the illumination light includes the steps of:
    moving the plant product in a first travel direction; and
    detecting the reflected light substantially along a line perpendicular to the first travel direction.

11. An apparatus for inspecting plant products for damage to the plant products, comprising:
    a first beam emitter for providing a first illumination light to a plant product to produce a narrow beam defining a line of light on said outer surface that is perpendicular to a travel direction of the plant product;
    a first beam detector for detecting with a narrow field of view overlapping said line of light on said outer surface substantially a single wavelength of first reflected light from the plant product without detecting light at other wavelengths and responsively producing a first reflection signal;

means for rotating the plant product about an axis parallel to said direction of travel and at a predetermined rotation rate; and a control unit for receiving first reflection signals and in response to reflected light from a plurality of detected narrow beams accumulated sequentially as the plant product is moved and rotated in a direction of travel, responsively assigning a damage category to the plant product; wherein the control unit determines at least one of a presence, an amount, and a severity of damage responsive to the first reflection signal solely at a single wavelength and assigns the damage category to the plant product responsive to the determination of damage.

12. The apparatus of claim 11, including:

a second beam emitter for providing a second illumination light to the plant product; and a second beam detector for detecting substantially a single wavelength of second reflected light from the plant product and responsively producing a second reflection signal; wherein the control unit receives at least one of each of first and second reflection signals and responsively assigns the damage category to the plant product.

13. The apparatus of claim 12, wherein the control unit generates an image of the plant product responsive to the first and second reflection signals.

14. The apparatus of claim 12, wherein the second beam emitter provides a second illumination light of substantially a single wavelength.

15. The apparatus of claim 12, wherein the second beam emitter is at least one of a laser, a light-emitting diode, a broad-spectrum lamp, and a broad-spectrum lamp including a filter and wherein the second beam detector is at least one of a photodiode, a camera, a camera including a filter, and a CCD sensor.

16. The apparatus of claim 12, wherein the second beam emitter is a laser of the diode type.

17. The apparatus of claim 12, wherein the single wavelength of the second reflected light is substantially within the range of 900 nm to 1100 nm.

18. The apparatus of claim 12, wherein the single wavelength of the second reflected light is 980 nm.

19. The apparatus of claim 12, wherein damage to the plant product reflects less of the second illumination light as second reflected light than does an undamaged outer surface of the plant product.

20. The apparatus of claim 12, wherein the second beam emitter provides a line of second illumination light perpendicular to a direction of plant product travel.

21. The apparatus of claim 20, wherein the second beam emitter provides the line of second illumination light by at least one of: scanning a point of second illumination light along a predetermined path, and passing the second illumination light from a second light source through an optical device to concurrently form a line of second illumination light.

22. The apparatus of claim 12, wherein the second beam detector detects a line of second reflected light perpendicular to a direction of plant product travel, and the control unit combines multiple first and second reflection signals to responsively generate a determination of damage for substantially an entire surface of the plant product.

23. The apparatus of claim 12, wherein the second beam detector detects an area of second reflected light.

24. The apparatus of claim 11, wherein the control unit generates an image of the plant product responsive to the first reflection signal.

25. The apparatus of claim 11, wherein the control unit includes a processor, a memory, and at least one software instruction.

26. The apparatus of claim 25, wherein the control unit includes software instructions for at least one of: beam emitter control, beam detector control, reflection signal storing, reflection signal combining, reflection signal analysis, image generation, damage assessment, damage category assignation, and plant product routing.

27. The apparatus of claim 11, including:

a conveyor system to carry one or more plant products past the first beam emitter and the first beam detector.

28. The apparatus of claim 27, wherein the conveyor system directs the plant product to one of two or more predetermined locations based upon the damage category of the plant product.

29. The apparatus of claim 11, wherein the first beam emitter provides a first illumination light of substantially a single wavelength.

30. The apparatus of claim 11, wherein the first beam emitter is at least one of a laser, a light-emitting diode, a broad-spectrum lamp, and a broad-spectrum lamp including a filter and wherein the first beam detector is at least one of a photodiode, a camera, a camera including a filter, and a CCD sensor.

31. The apparatus of claim 11, wherein the first beam emitter is a laser of the diode type.

32. The apparatus of claim 11, wherein the single wavelength of the first reflected light is substantially within the range of 900 nm to 1100 nm.

33. The apparatus of claim 12, wherein the single wavelength of the first reflected light is 980 nm.

34. The apparatus of claim 11, wherein the plant product is at least one of a non-citrus fruit, a vegetable, a legume, and a citrus fruit.

35. The apparatus of claim 11, wherein the damage is at least one of decay, pre-harvest mechanical damage, post-harvest mechanical damage, blemish, stems, blossoms, firmness, or water content of the plant product.

36. The apparatus of claim 11, wherein damage to the plant product reflects less of the first illumination light as first reflected light than does an undamaged outer surface of the plant product.

37. The apparatus of claim 11, wherein the first beam emitter provides a line of first illumination light perpendicular to a direction of plant product travel.

38. The apparatus of claim 37, wherein the first beam emitter provides the line of first illumination light by at least one of: scanning a point of first illumination light along a predetermined path, and passing the first illumination light from a first light source through an optical device to concurrently form a line of first illumination light.

39. The apparatus of claim 11, wherein the first beam detector detects a line of first reflected light perpendicular to a direction of plant product travel, and the control unit combines multiple first reflection signals to responsively generate a determination of damage of the plant product.

40. The apparatus of claim 11, wherein the first beam detector detects an area of first reflected light.

41. An apparatus for sorting plant products based on damage, comprising:
- a first beam emitter for providing a first illumination light to a plant product to produce a narrow beam defining a line of light on said outer surface that is perpendicular to a travel direction of the plant product;
- a first beam detector for detecting with a narrow field of view overlapping said line of light on said outer surface substantially a single wavelength of first reflected light from the plant product without detecting light at other wavelengths and responsively producing a first reflection signal;
- means for rotating the plant product about an axis parallel to said direction of travel and at a predetermined rotation rate;
- means for determining, in response to reflected light from a plurality of detected narrow beams accumulated sequentially as the plant product is moved and rotated in a direction of travel, and responsive to substantially a single wavelength of light_solely on the basis of a measurement at the single wavelength and without detecting light at other wavelengths, at least one of a presence, an amount, and a severity of damage to a surface of the plant product; and
- means for sorting the plant products into one of two or more damage categories responsive to the determination of damage.

42. The apparatus of claim 41, wherein the means for determining includes at least one of means for generating an illumination light of substantially a single wavelength, and means for detecting a reflected light of substantially a single wavelength.

43. The apparatus of claim 41, wherein the single wavelength is substantially within the range of 900 nm to 1100 nm.

44. The apparatus of claim 41, wherein the plant product is at least one of a non-citrus fruit, a vegetable, a legume, and a citrus fruit.

45. The apparatus of claim 41, wherein the damage is at least one of decay, pre-harvest mechanical damage, post-harvest mechanical damage, blemish, stems, blossoms, firmness, or water content of the plant product.

46. The apparatus of claim 41, wherein damage to the plant product reflects less of the single wavelength of light than does an undamaged outer surface of the plant product.

47. The apparatus of claim 41, including means for moving the plant product relative to the means for determining such that a surface of the plant product is exposed to the means for determining.

48. An apparatus for scanning a plant product to detect damage to the plant product, comprising:
- at least one beam emitter, each for providing an illumination light to the plant product, each emitter operative to produce a narrow beam defining a line of light on said outer surface that is perpendicular to a travel direction of the plant product;
- at least one beam detector, each for detecting with a narrow field of view overlapping said line of light on said outer surface a reflected light from the plant product without detecting light at other wavelengths and responsively producing at least one reflection signal; and
- a control unit for receiving the at least one reflection signal, and in response to reflected light from a plurality of detected narrow beams accumulated sequentially as the plant product is moved and rotated in a direction of travel, and responsively generating a plant product image;
- wherein the reflected light has substantially a single wavelength and wherein damage to the plant product is detected responsive to the plant product image generated solely by light reflected at the single wavelength.

49. The apparatus of claim 48, wherein the beam emitter is a laser.

50. The apparatus of claim 48, wherein the single wavelength is substantially within the range of 900 nm to 1100 nm.

51. The apparatus of claim 48, wherein the control unit combines multiple reflection signals to produce a plant product image of substantially an entire surface of the plant product.

52. The apparatus of claim 48, wherein the at least one beam detector detects the reflected light substantially along a detection line.

53. The apparatus of claim 52, wherein the plant product is moving along a product line substantially perpendicular to the detection line.

* * * * *